US012140487B2

(12) United States Patent
Messerly

(10) Patent No.: US 12,140,487 B2
(45) Date of Patent: Nov. 12, 2024

(54) OPTICAL FIBER-BASED MEDICAL DEVICE TRACKING AND MONITORING SYSTEM

(71) Applicant: Bard Access System, Inc., Salt Lake City, UT (US)

(72) Inventor: Shayne Messerly, Kaysville, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 774 days.

(21) Appl. No.: 15/947,267

(22) Filed: Apr. 6, 2018

(65) Prior Publication Data
US 2018/0289927 A1    Oct. 11, 2018

Related U.S. Application Data

(60) Provisional application No. 62/483,195, filed on Apr. 7, 2017.

(51) Int. Cl.
*A61B 5/00* (2006.01)
*A61B 5/06* (2006.01)
(Continued)

(52) U.S. Cl.
CPC ............ *G01L 5/161* (2013.01); *A61B 5/0084* (2013.01); *A61B 5/066* (2013.01); *A61B 5/6852* (2013.01);
(Continued)

(58) Field of Classification Search
CPC .......... A61M 25/0102; A61M 25/0026; A61M 2025/0034; A61M 2025/0166;
(Continued)

(56) References Cited

U.S. PATENT DOCUMENTS

| 4,813,429 A | 3/1989 | Eshel et al. |
| 5,099,845 A | 3/1992 | Besz et al. |

(Continued)

FOREIGN PATENT DOCUMENTS

| CN | 101132730 A | 2/2008 |
| CN | 111265309 A | 6/2020 |

(Continued)

OTHER PUBLICATIONS

PCT/US2018/026493 filed Apr. 6, 2018 International Search Report and Written Opinion dated Jun. 22, 2018.

(Continued)

*Primary Examiner* — Katherine L Fernandez
*Assistant Examiner* — Brooke Lyn Klein
(74) *Attorney, Agent, or Firm* — Rutan & Tucker LLP

(57) ABSTRACT

A placement system for tracking, placing, and monitoring a catheter assembly or other medical device inserted into a body of a patient is disclosed. The placement system utilizes optical fiber-based strain sensors to assist with catheter placement. In one embodiment, the placement system comprises a console including a processor and a plurality of optical fiber-based strain sensors included with the catheter. A light source is also included and configured to operably connect with the strain sensors and produce outgoing optical signals incident on the strain sensors. A photodetector is included and configured to operably connect with the strain sensors and receive return optical signals from the strain sensors. A processor is configured to process data from the return optical signals. The data relates to an aspect of the catheter. A user interface such as a display is configured to communicate information relating to the aspect of the catheter.

1 Claim, 7 Drawing Sheets

(51) Int. Cl.

| | |
|---|---|
| *A61B 8/12* | (2006.01) |
| *A61B 34/20* | (2016.01) |
| *A61M 25/00* | (2006.01) |
| *A61M 25/01* | (2006.01) |
| *G01L 1/24* | (2006.01) |
| *G01L 5/161* | (2020.01) |
| *A61B 5/01* | (2006.01) |
| *A61B 5/0215* | (2006.01) |

(52) U.S. Cl.
CPC ............... *A61B 8/12* (2013.01); *A61B 34/20* (2016.02); *A61M 25/0026* (2013.01); *A61M 25/0102* (2013.01); *G01L 1/242* (2013.01); *G01L 1/246* (2013.01); *A61B 5/01* (2013.01); *A61B 5/0215* (2013.01); *A61B 2034/2055* (2016.02); *A61B 2034/2061* (2016.02); *A61B 2562/0266* (2013.01); *A61M 2025/0034* (2013.01); *A61M 2025/0166* (2013.01)

(58) Field of Classification Search
CPC ....... A61B 34/20; A61B 5/0084; A61B 5/066; A61B 5/6852; A61B 8/12; A61B 2034/2055; A61B 2034/2061; A61B 5/01; A61B 5/0215; A61B 2562/0266; G01L 1/242; G01L 1/246; G01L 5/161
See application file for complete search history.

(56) References Cited

U.S. PATENT DOCUMENTS

| | | |
|---|---|---|
| 5,163,935 A | 11/1992 | Black et al. |
| 5,207,672 A | 5/1993 | Roth et al. |
| 5,211,165 A | 5/1993 | Dumoulin et al. |
| 5,275,151 A | 1/1994 | Shockey et al. |
| 5,280,786 A | 1/1994 | Wlodarczyk et al. |
| 5,423,321 A | 6/1995 | Fontenot |
| 5,454,807 A | 10/1995 | Lennox et al. |
| 5,517,997 A | 5/1996 | Fontenot |
| 5,622,170 A | 4/1997 | Schulz |
| 5,740,808 A | 4/1998 | Panescu et al. |
| 5,872,879 A | 2/1999 | Hamm |
| 5,873,842 A | 2/1999 | Brennen et al. |
| 5,879,306 A | 3/1999 | Fontenot et al. |
| 5,906,579 A | 5/1999 | Vander Salm et al. |
| 6,069,698 A | 5/2000 | Ozawa et al. |
| 6,081,741 A | 6/2000 | Hollis |
| 6,178,346 B1 | 1/2001 | Amundson et al. |
| 6,208,887 B1 | 3/2001 | Clarke |
| 6,319,227 B1 | 11/2001 | Mansouri-Ruiz |
| 6,343,227 B1 | 1/2002 | Crowley |
| 6,398,721 B1 | 6/2002 | Nakamura et al. |
| 6,485,482 B1 | 11/2002 | Belef |
| 6,564,089 B2 | 5/2003 | Izatt et al. |
| 6,593,884 B1 | 7/2003 | Gilboa et al. |
| 6,597,941 B2 | 7/2003 | Fontenot et al. |
| 6,650,923 B1 | 11/2003 | Lesh et al. |
| 6,685,666 B1 | 2/2004 | Fontenot |
| 6,687,010 B1 | 2/2004 | Horii et al. |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 7,132,645 B2 | 11/2006 | Korn |
| 7,273,056 B2 | 9/2007 | Wilson et al. |
| 7,344,533 B2 | 3/2008 | Pearson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 | 5/2009 | Ainsworth et al. |
| 7,587,236 B2 | 9/2009 | Demos et al. |
| 7,603,166 B2 | 10/2009 | Casscells, III et al. |
| 7,729,735 B1 | 6/2010 | Burchman |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,054,469 B2 | 11/2011 | Nakabayashi et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,187,189 B2 | 5/2012 | Jung et al. |
| 8,267,932 B2 | 9/2012 | Baxter et al. |
| 8,369,932 B2 | 2/2013 | Cinbis et al. |
| 8,388,541 B2 | 3/2013 | Messerly et al. |
| 8,571,640 B2 | 10/2013 | Holman |
| 8,597,315 B2 | 12/2013 | Snow et al. |
| 8,700,358 B1 | 4/2014 | Parker, Jr. |
| 8,781,555 B2 * | 7/2014 | Burnside ............... A61B 5/042 |
| | | 600/424 |
| 8,798,721 B2 | 8/2014 | Dib |
| 8,968,331 B1 | 3/2015 | Sochor |
| 8,979,871 B2 | 3/2015 | Tyc et al. |
| 9,060,687 B2 | 6/2015 | Yamanaka et al. |
| 9,206,309 B2 | 12/2015 | Appleby et al. |
| 9,360,630 B2 | 6/2016 | Jenner et al. |
| 9,504,392 B2 | 11/2016 | Caron et al. |
| 9,560,954 B2 | 2/2017 | Jacobs et al. |
| 9,622,706 B2 | 4/2017 | Dick et al. |
| 9,678,275 B1 | 6/2017 | Griffin |
| 10,231,753 B2 | 3/2019 | Burnside et al. |
| 10,258,240 B1 | 4/2019 | Eberle et al. |
| 10,327,830 B2 | 6/2019 | Grant et al. |
| 10,349,890 B2 | 7/2019 | Misener et al. |
| 10,492,876 B2 | 12/2019 | Anastassiou et al. |
| 10,568,586 B2 | 2/2020 | Begin et al. |
| 10,631,718 B2 | 4/2020 | Petroff et al. |
| 10,992,078 B2 | 4/2021 | Thompson et al. |
| 11,123,047 B2 | 9/2021 | Jaffer et al. |
| 11,525,670 B2 | 12/2022 | Messerly et al. |
| 2002/0198457 A1 | 12/2002 | Tearney et al. |
| 2003/0092995 A1 | 5/2003 | Thompson |
| 2004/0242995 A1 | 12/2004 | Maschke |
| 2005/0033264 A1 | 2/2005 | Redinger |
| 2005/0261598 A1 | 11/2005 | Banet et al. |
| 2005/0278010 A1 | 12/2005 | Richardson |
| 2006/0013523 A1 | 1/2006 | Childers et al. |
| 2006/0015136 A1 | 1/2006 | Besselink |
| 2006/0036164 A1 * | 2/2006 | Wilson ..................... A61B 5/06 |
| | | 600/424 |
| 2006/0189959 A1 * | 8/2006 | Schneiter ............ A61M 25/007 |
| | | 604/508 |
| 2006/0200049 A1 | 9/2006 | Leo et al. |
| 2006/0241395 A1 | 10/2006 | Kruger et al. |
| 2006/0241492 A1 | 10/2006 | Boese et al. |
| 2007/0156019 A1 * | 7/2007 | Larkin .................. B25J 19/025 |
| | | 600/104 |
| 2007/0201793 A1 | 8/2007 | Askins et al. |
| 2007/0287886 A1 | 12/2007 | Saadat |
| 2007/0299425 A1 | 12/2007 | Waner et al. |
| 2008/0039715 A1 | 2/2008 | Wilson et al. |
| 2008/0082004 A1 | 4/2008 | Banet et al. |
| 2008/0172119 A1 | 7/2008 | Yamasaki et al. |
| 2008/0183128 A1 * | 7/2008 | Morriss ............. A61M 25/0068 |
| | | 604/35 |
| 2009/0054908 A1 | 2/2009 | Zand et al. |
| 2009/0062634 A1 | 3/2009 | Say et al. |
| 2009/0118612 A1 | 5/2009 | Grunwald et al. |
| 2009/0137952 A1 | 5/2009 | Ramamurthy et al. |
| 2009/0234328 A1 * | 9/2009 | Cox ........................ A61B 5/287 |
| | | 604/523 |
| 2009/0304582 A1 | 12/2009 | Rousso et al. |
| 2009/0314925 A1 | 12/2009 | Van Vorhis et al. |
| 2010/0016729 A1 | 1/2010 | Futrell |
| 2010/0030063 A1 | 2/2010 | Lee et al. |
| 2010/0063534 A1 | 3/2010 | Kugler et al. |
| 2010/0114115 A1 | 5/2010 | Schlesinger et al. |
| 2010/0286531 A1 | 11/2010 | Ryan et al. |

(56) References Cited

U.S. PATENT DOCUMENTS

| | | |
|---|---|---|
| 2010/0312095 A1 | 12/2010 | Jenkins et al. |
| 2011/0144481 A1 | 6/2011 | Feer et al. |
| 2011/0166442 A1 | 7/2011 | Sarvazyan |
| 2011/0172680 A1 | 7/2011 | Younge et al. |
| 2011/0237958 A1 | 9/2011 | Onimura |
| 2011/0245662 A1 | 10/2011 | Eggers et al. |
| 2011/0295108 A1 | 12/2011 | Cox et al. |
| 2011/0313280 A1 | 12/2011 | Govari et al. |
| 2012/0046562 A1* | 2/2012 | Powers .............. A61B 5/7246 600/509 |
| 2012/0065481 A1 | 3/2012 | Hunter et al. |
| 2012/0101413 A1 | 4/2012 | Beetel et al. |
| 2012/0136242 A1 | 5/2012 | Qi et al. |
| 2012/0143029 A1 | 6/2012 | Silverstein et al. |
| 2012/0184827 A1 | 7/2012 | Shwartz et al. |
| 2012/0184955 A1 | 7/2012 | Pivotto et al. |
| 2012/0289783 A1 | 11/2012 | Duindam et al. |
| 2012/0321243 A1 | 12/2012 | Younge et al. |
| 2013/0072943 A1 | 3/2013 | Parmar |
| 2013/0096482 A1 | 4/2013 | Bertrand et al. |
| 2013/0104884 A1 | 5/2013 | Vazales et al. |
| 2013/0188855 A1 | 7/2013 | Desjardins et al. |
| 2013/0204124 A1 | 8/2013 | Duindam et al. |
| 2013/0211246 A1 | 8/2013 | Parasher |
| 2013/0296693 A1 | 11/2013 | Wenzel et al. |
| 2013/0310668 A1 | 11/2013 | Young |
| 2013/0317372 A1 | 11/2013 | Eberle et al. |
| 2013/0324840 A1 | 12/2013 | Zhongping et al. |
| 2014/0121468 A1 | 5/2014 | Eichenholz |
| 2014/0221829 A1 | 8/2014 | Maitland et al. |
| 2014/0275997 A1 | 9/2014 | Chopra et al. |
| 2015/0029511 A1 | 1/2015 | T Hooft et al. |
| 2015/0031987 A1 | 1/2015 | Pameijer et al. |
| 2015/0080688 A1 | 3/2015 | Cinbis et al. |
| 2015/0099979 A1 | 4/2015 | Caves et al. |
| 2015/0119700 A1 | 4/2015 | Liang et al. |
| 2015/0141854 A1 | 5/2015 | Eberle et al. |
| 2015/0164571 A1 | 6/2015 | Saadat |
| 2015/0190221 A1 | 7/2015 | Schaefer et al. |
| 2015/0209113 A1 | 7/2015 | Burkholz et al. |
| 2015/0209117 A1 | 7/2015 | Flexman et al. |
| 2015/0254526 A1 | 9/2015 | Denissen |
| 2015/0320977 A1* | 11/2015 | Vitullo .............. A61M 25/0113 604/510 |
| 2016/0018602 A1 | 1/2016 | Govari et al. |
| 2016/0067449 A1 | 3/2016 | Misener et al. |
| 2016/0102969 A1 | 4/2016 | Verstege et al. |
| 2016/0166326 A1* | 6/2016 | Bakker .............. A61N 1/372 600/544 |
| 2016/0166341 A1 | 6/2016 | Iordachita et al. |
| 2016/0184020 A1 | 6/2016 | Kowalewski et al. |
| 2016/0354038 A1 | 12/2016 | Demirtas et al. |
| 2017/0020394 A1 | 1/2017 | Harrington |
| 2017/0079681 A1 | 3/2017 | Burnside et al. |
| 2017/0082806 A1 | 3/2017 | Van Der Mark et al. |
| 2017/0173349 A1 | 6/2017 | Pfleiderer et al. |
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1* | 9/2017 | Ma .............. A61B 5/0059 |
| 2017/0273628 A1 | 9/2017 | Ofek et al. |
| 2017/0290563 A1 | 10/2017 | Cole et al. |
| 2018/0095231 A1 | 4/2018 | Lowell et al. |
| 2018/0113038 A1* | 4/2018 | Janabi-Sharifi ......... G01L 1/246 |
| 2018/0140170 A1 | 5/2018 | Van Putten et al. |
| 2018/0239124 A1 | 8/2018 | Naruse et al. |
| 2018/0240237 A1 | 8/2018 | Donhowe et al. |
| 2018/0250088 A1 | 9/2018 | Brennan et al. |
| 2018/0264227 A1 | 9/2018 | Flexman et al. |
| 2018/0289390 A1 | 10/2018 | Amorizzo et al. |
| 2018/0289927 A1 | 10/2018 | Messerly |
| 2018/0339134 A1 | 11/2018 | Leo |
| 2018/0360545 A1 | 12/2018 | Cole et al. |
| 2019/0059743 A1* | 2/2019 | Ramachandran ...... A61B 5/061 |
| 2019/0110844 A1 | 4/2019 | Misener et al. |
| 2019/0237902 A1 | 8/2019 | Thompson et al. |
| 2019/0307331 A1 | 10/2019 | Saadat et al. |
| 2019/0321110 A1 | 10/2019 | Grunwald et al. |
| 2019/0343424 A1 | 11/2019 | Blumenkranz et al. |
| 2019/0357875 A1 | 11/2019 | Qi et al. |
| 2019/0374130 A1 | 12/2019 | Bydlon et al. |
| 2020/0030575 A1 | 1/2020 | Bogusky et al. |
| 2020/0046434 A1 | 2/2020 | Graetzel et al. |
| 2020/0054399 A1 | 2/2020 | Duindam et al. |
| 2020/0188036 A1 | 6/2020 | Ding et al. |
| 2020/0315770 A1 | 10/2020 | Dupont et al. |
| 2021/0015470 A1 | 1/2021 | Prisco et al. |
| 2021/0023341 A1 | 1/2021 | Decheek et al. |
| 2021/0045814 A1 | 2/2021 | Thompson et al. |
| 2021/0068911 A1 | 3/2021 | Walker et al. |
| 2021/0298680 A1 | 3/2021 | Sowards et al. |
| 2021/0244311 A1 | 8/2021 | Zhao et al. |
| 2021/0268229 A1 | 9/2021 | Sowards et al. |
| 2021/0271035 A1 | 9/2021 | Sowards et al. |
| 2021/0275257 A1 | 9/2021 | Prior et al. |
| 2021/0330399 A1 | 10/2021 | Netravali et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0011192 A1 | 1/2022 | Misener et al. |
| 2022/0034733 A1 | 2/2022 | Misener et al. |
| 2022/0096796 A1 | 3/2022 | McLaughlin et al. |
| 2022/0110695 A1 | 4/2022 | Sowards et al. |
| 2022/0152349 A1 | 5/2022 | Sowards et al. |
| 2022/0160209 A1 | 5/2022 | Sowards et al. |
| 2022/0172354 A1 | 6/2022 | Misener et al. |
| 2022/0211442 A1 | 7/2022 | McLaughlin et al. |
| 2022/0233246 A1 | 7/2022 | Misener et al. |
| 2022/0369934 A1 | 11/2022 | Sowards et al. |
| 2023/0081198 A1 | 3/2023 | Sowards et al. |
| 2023/0097431 A1 | 3/2023 | Sowards et al. |
| 2023/0101030 A1 | 3/2023 | Misener et al. |
| 2023/0108604 A1 | 4/2023 | Messerly et al. |
| 2023/0126813 A1 | 4/2023 | Sowards et al. |
| 2023/0243715 A1 | 8/2023 | Misener et al. |
| 2023/0248444 A1 | 8/2023 | Misener et al. |
| 2023/0251150 A1 | 8/2023 | Misener et al. |
| 2023/0337985 A1 | 10/2023 | Sowards et al. |
| 2023/0414112 A1 | 12/2023 | Misener et al. |
| 2024/0000515 A1 | 1/2024 | Misener et al. |
| 2024/0050708 A1 | 2/2024 | Misener |
| 2024/0099659 A1 | 3/2024 | Sowards et al. |
| 2024/0108856 A1 | 4/2024 | Messerly |
| 2024/0216077 A1 | 7/2024 | Thompson et al. |

FOREIGN PATENT DOCUMENTS

| | | | |
|---|---|---|---|
| CN | 113080937 A | 7/2021 | |
| DE | 102016109601 A1 | 11/2017 | |
| EP | 2240111 A2 | 10/2010 | |
| EP | 2907445 A1 | 8/2015 | |
| EP | 3545849 A1 | 10/2019 | |
| EP | 3705020 A1 | 9/2020 | |
| JP | 7366562 B2 | 10/2023 | |
| KR | 20190098512 A | 8/2019 | |
| WO | 99/64099 A1 | 12/1999 | |
| WO | 1999064099 A1 | 12/1999 | |
| WO | 2006122001 A2 | 11/2006 | |
| WO | 2009/155325 A2 | 12/2009 | |
| WO | 2011121516 A2 | 10/2011 | |
| WO | WO-2011141830 A1 * | 11/2011 | .............. A61B 6/12 |
| WO | 2011150376 A1 | 12/2011 | |
| WO | 2012064769 A2 | 5/2012 | |
| WO | 2015044930 A1 | 4/2015 | |
| WO | 2015074045 A2 | 5/2015 | |
| WO | 2016038492 A1 | 3/2016 | |
| WO | 2016/061431 A1 | 4/2016 | |
| WO | 2016051302 A1 | 4/2016 | |
| WO | 2016149819 A1 | 9/2016 | |
| WO | 2019037071 A1 | 2/2019 | |
| WO | 2019/046769 A1 | 3/2019 | |
| WO | 2019070423 A1 | 4/2019 | |

(56) References Cited

FOREIGN PATENT DOCUMENTS

| | | |
|---|---|---|
| WO | 2019230713 A1 | 12/2019 |
| WO | 2020/182997 A1 | 9/2020 |
| WO | 2021030092 A1 | 2/2021 |
| WO | 2021108688 A1 | 6/2021 |
| WO | 2021108697 A1 | 6/2021 |
| WO | 2021/138096 A1 | 7/2021 |
| WO | 2021216089 A1 | 10/2021 |
| WO | 2022/031613 A1 | 2/2022 |
| WO | 2022/081723 A1 | 4/2022 |
| WO | 2022150411 A1 | 7/2022 |
| WO | 2022/164902 A1 | 8/2022 |
| WO | 2022/245987 A1 | 11/2022 |
| WO | 2023043954 A1 | 3/2023 |
| WO | 2023049443 A1 | 3/2023 |
| WO | 2023055810 A1 | 4/2023 |
| WO | 2023076143 A1 | 5/2023 |
| WO | 2023211752 A1 | 11/2023 |
| WO | 2024006384 A1 | 1/2024 |
| WO | 2024006441 A1 | 1/2024 |
| WO | 2024064334 A1 | 3/2024 |

OTHER PUBLICATIONS

PCT/US2020/044801 filed Aug. 3, 2020 International Search Report and Written Opinion dated Oct. 26, 2020.
PCT/US2021/019713 filed Feb. 25, 2021 International Search Report and Written Opinion dated Jul. 6, 2021.
PCT/US2021/020079 filed Feb. 26, 2021 International Search Report and Written Opinion dated Jun. 4, 2021.
PCT/US2020/062396 filed Nov. 25, 2020 International Search Report and Written Opinion dated Mar. 2, 2021.
PCT/US2020/062407 filed Nov. 25, 2020 International Search Report and Written Opinion dated Mar. 11, 2021.
PCT/US2021/020732 filed Mar. 3, 2021 International Search Report and Written Opinion dated Jul. 5, 2021.
PCT/US2021/038899 filed Jun. 24, 2021 International Search Report and Written Opinion dated Oct. 6, 2021.
PCT/US2021/038954 filed Jun. 24, 2021 International Search Report and Written Opinion dated Oct. 28, 2021.
PCT/US2021/041128 filed Jul. 9, 2021 International Search Report and Written Opinion dated Oct. 25, 2021.
PCT/US2021/044216 filed Aug. 2, 2021 International Search Report and Written Opinion dated Nov. 18, 2021.
U.S. Appl. No. 17/185,777, filed Feb. 25, 2021 Non-Final Office Action dated Feb. 9, 2022.
PCT/US2021/054802 filed Oct. 13, 2021 International Search Report and Written Opinion dated Feb. 2, 2022.
PCT/US2021/060849 filed Nov. 24, 2021 International Search Report and Written Opinion dated Mar. 9, 2022.
PCT/US2022/011347 filed Jan. 5, 2022 International Search Report and Written Opinion dated May 3, 2022.
PCT/US2022/013897 filed Jan. 26, 2022 International Search Report and Written Opinion dated May 11, 2022.
U.S. Appl. No. 17/105,259, filed Nov. 25, 2020, Notice of Allowance dated Jul. 20, 2022.
U.S. Appl. No. 17/371,993, filed Jul. 9, 2021 Non-Final Office Action dated Jul. 12, 2022.
PCT/US2023/033471 filed Sep. 22, 2023 International Search Report and Written Opinion dated Dec. 21, 2023.
U.S. Appl. No. 16/984,104, filed Aug. 3, 2020 Notice of Allowance dated Nov. 21, 2023.
U.S. Appl. No. 17/500,678, filed Oct. 13, 2021 Advisory Action dated Dec. 7, 2023.
U.S. Appl. No. 17/500,678, filed Oct. 13, 2021 Non-Final Office Action dated Jan. 19, 2024.
U.S. Appl. No. 18/079,653, filed Dec. 12, 2022 Non-Final Office Action dated Feb. 6, 2024.
U.S. Appl. No. 18/135,337, filed Apr. 17, 2023 Non-Final Office Action dated Dec. 22, 2023.
U.S. Appl. No. 17/569,350, filed Jan. 5, 2022 Non-Final Office Action dated Jan. 8, 2024.
PCT/US2022/029894 filed May 18, 2022, International Search Report and Written Opinion dated Sep. 1, 2022.
U.S. Appl. No. 17/357,561, filed Jun. 24, 2021 Non-Final Office Action dated Aug. 11, 2022.
U.S. Appl. No. 17/392,002, filed Aug. 2, 2021, Non-Final Office Action dated Sep. 12, 2022.
EP 20853352.1 filed Mar. 7, 2022 Extended European Search Report dated Jul. 27, 2023.
PCT/US2023/019239 filed Apr. 20, 2023 International Search Report and Written Opinion dated Jul. 20, 2023.
U.S. Appl. No. 16/984,104, filed Aug. 3, 2020 Non-Final Office Action dated Jun. 22, 2023.
U.S. Appl. No. 17/105,310, filed Nov. 25, 2020 Notice of Allowance dated Aug. 2, 2023.
U.S. Appl. No. 17/357,186, filed Jun. 24, 2021 Non Final Office Action dated May 30, 2023.
U.S. Appl. No. 17/484,960, filed Sep. 24, 2021 Notice of Allowance dated Apr. 12, 2024.
U.S. Appl. No. 17/569,350, filed Jan. 5, 2022 Final Office Action dated Apr. 23, 2024.
U.S. Appl. No. 17/747,903, filed May 18, 2022 Restriction Requirement dated May 28, 2024.
U.S. Appl. No. 18/132,623, filed Apr. 10, 2023, Non-Final Office Action dated May 3, 2024.
U.S. Appl. No. 18/135,337, filed Apr. 17, 2023 Notice of Allowance dated Mar. 8, 2024.
Fiber Optic RealShape (FORS) technology—research. Philips. (Oct. 18, 2018). Retrieved Feb. 28, 2023, from https:// www.philips.com/a-w/research/research-programs/fors.html (Year: 2018).
U.S. Appl. No. 16/984,104, filed Aug. 3, 2020 Restriction Requirement dated Mar. 13, 2023.
U.S. Appl. No. 17/105,310, filed Nov. 25, 2020 Non-Final Office Action dated Feb. 22, 2023.
U.S. Appl. No. 17/357,186, filed Jun. 24, 2021 Restriction Requirement dated Mar. 7, 2023.
U.S. Appl. No. 17/392,002, filed Aug. 2, 2021, Corrected Notice of Allowability dated Feb. 23, 2023.
U.S. Appl. No. 17/500,678, filed Oct. 13, 2021 Non-Final Office Action dated Mar. 15, 2023.
Jackle Sonja et al. "Three-dimensional guidance including shape sensing of a stentgraft system for endovascular aneurysm repair." International Journal of Computer Assisted Radiology and Surgery, Springer DE. vol. 15, No. 6, May 7, 2020.
PCT/US2022/043706 filed Sep. 16, 2022 International Search Report and Written Opinion dated Nov. 24, 2022.
PCT/US2022/044696 filed Sep. 26, 2022 International Search Report and Written Opinion dated Jan. 23, 2023.
PCT/US2022/045051 filed Sep. 28, 2022 International Search Report and Written Opinion dated Jan. 2, 2023.
U.S. Appl. No. 17/357,561, filed Jun. 24, 2021 Notice of Allowance dated Dec. 9, 2022.
U.S. Appl. No. 17/371,993, filed Jul. 9, 2021 Notice of Allowance dated Nov. 3, 2022.
U.S. Appl. No. 17/392,002, filed Aug. 2, 2021, Notice of Allowance dated Jan. 19, 2023.
Dziuda L et al: "Monitoring Respiration and Cardiac Activity Using Fiber Bragg Grating-Based Sensor", IEEE Transactions on Biomedical Engineering vol. 59, No. 7, Jul. 2012 pp. 1934-1942.
Dziuda L et al: "Fiber-optic sensor for monitoring respiration and cardiac activity", 2011 IEEE Sensors Proceedings : Limerick, Ireland, Oct. 2011 pp. 413-416.
EP 20893677.3 filed Jun. 22, 2022 Extended European Search Report dated Oct. 13, 2023.
EP 20894633.5 filed Jun. 22, 2022 Extended European Search Report dated Oct. 16, 2023.
PCT/US2023/026487 filed Jun. 28, 2023 International Search Report and Written Opinion dated Sep. 6, 2023.
PCT/US2023/026581 filed Jun. 29, 2023 International Search Report and Written Opinion dated Oct. 27, 2023.
U.S. Appl. No. 16/984,104, filed Aug. 3, 2020 Final Office Action dated Sep. 21, 2023.

(56) References Cited

OTHER PUBLICATIONS

U.S. Appl. No. 17/357,186, filed Jun. 24, 2021 Notice of Allowance dated Aug. 23, 2023.
U.S. Appl. No. 17/484,960, filed Sep. 24, 2021 Non-Final Office Action dated Oct. 5, 2023.
U.S. Appl. No. 17/500,678, filed Oct. 13, 2021 Final Office Action dated Sep. 21, 2023.
U.S. Appl. No. 17/569,350, filed Jan. 5, 2022 Advisory Action dated Jul. 12, 2024.
U.S. Appl. No. 17/747,903, filed May 18, 2022 Non-Final Office Action dated Aug. 15, 2024.
U.S. Appl. No. 17/955,019, filed Sep. 28, 2022 Restriction Requirement dated Jun. 6, 2024.
U.S. Appl. No. 18/079,653, filed Dec. 12, 2022 Notice of Allowance dated Jun. 4, 2024.
U.S. Appl. No. 18/132,231, filed Apr. 7, 2023 Non-Final Office Action dated Jul. 12, 2024.
U.S. App. No. 18/538,111 filed Dec. 13, 2023 Non-Final Office Action dated Aug. 9, 2024.
U.S. Appl. No. 17/569,350, filed Jan. 5, 2022 Non-Final Office Action dated Aug. 12, 2024.
U.S. Appl. No. 17/971,873, filed Oct. 24, 2022 Non-Final Office Action dated Jun. 6, 2024.

\* cited by examiner

OPTICAL FIBER-BASED MEDICAL DEVICE TRACKING AND MONITORING SYSTEM

CROSS-REFERENCE TO RELATED APPLICATIONS

This application claims the benefit of U.S. Provisional Application No. 62/483,195, filed Apr. 7, 2017, and titled "Optical Fiber-Based Medical Device Tracking and Monitoring System," which is incorporated herein by reference in its entirety.

BRIEF SUMMARY

Briefly summarized, embodiments of the present invention are directed to a placement system for tracking, placing, and monitoring a catheter assembly or other medical device inserted into a body of a patient. The placement system utilizes optical fiber-based strain sensors to ascertain information regarding the catheter assembly during and/or after insertion into the patient's body.

In one embodiment, the placement system comprises a plurality of optical fiber-based strain sensors included with the medical device. A laser light source (or other suitable light source) is also included and configured to operably connect with the strain sensors and produce outgoing optical signals incident on the strain sensors. A photodetector is included and configured to operably connect with the strain sensors and receive return optical signals from the strain sensors. A processor is configured to process data from the return optical signals. The data relates to an aspect of the medical device. A user interface such as a display is configured to communicate information relating to the aspect of the medical device.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Figure 1A:
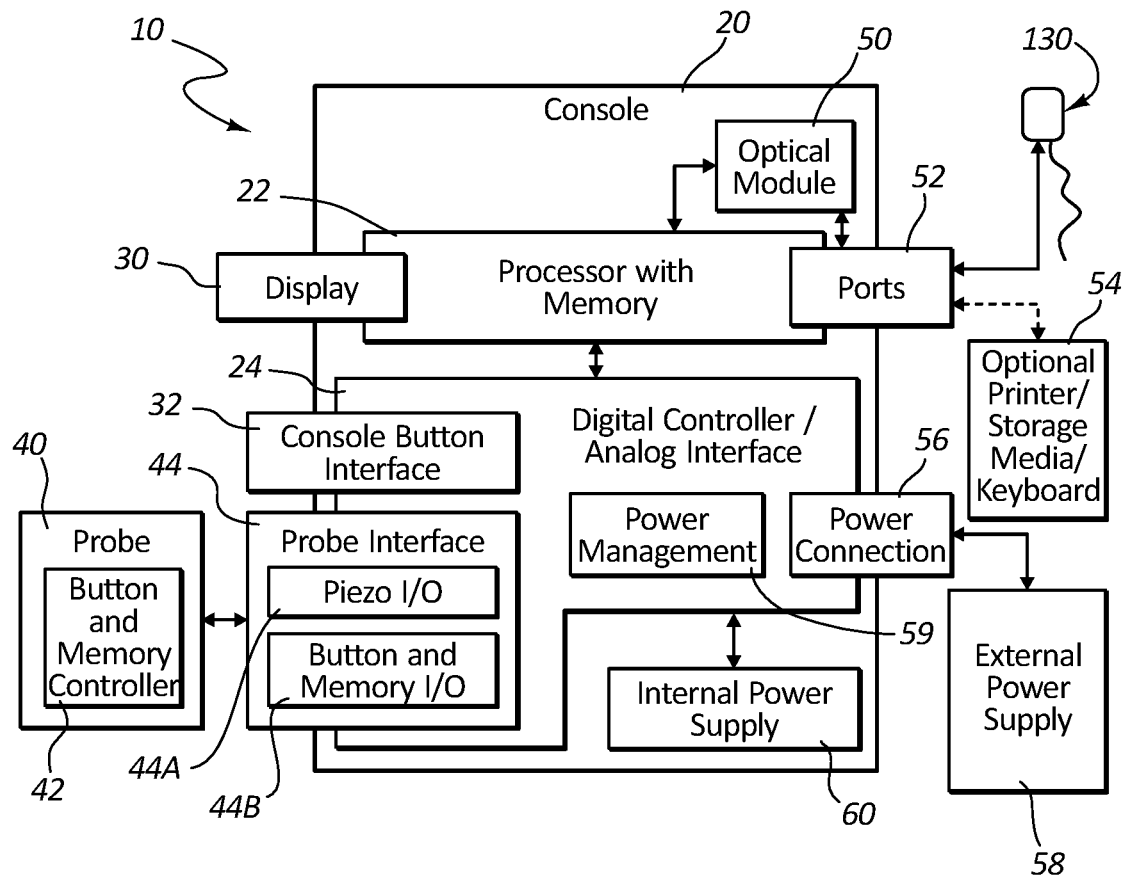
FIGS. 1A and 1B are various block diagram views of a placement system for guiding and placing a medical device into a body of a patient.

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a placement system for tracking, placing, and monitoring a medical device inserted into a body of a patient. An example of such a medical device is a catheter assembly that is inserted into a vein or other vessel of the patient so as to infuse or aspirate fluids through one or more lumens defined by the catheter for the patient. The system utilizes optical fiber-based strain sensors in one embodiment to ascertain information regarding the catheter or other medical device during and/or after insertion into the patient's body.

In one embodiment, the strain sensors include fiber Bragg grating ("FBG") sensors distributed along an optical fiber disposed in/on the catheter assembly (or other medical device). An outgoing optical signal produced by a swept laser is incident on each of the FBG sensors in the fiber, which each respond, producing a return optical signal. A processor of the placement system processes the return optical signal with predetermined algorithms to determine the strain and other data of each of the FBG sensors. The data is communicated to a user of the system and can provide information regarding the medical device, its position within the body, the 2-D and 3-D shape of the medical device along its length (e.g., bending, torsion), device orientation (including malposition or device kinking), body temperature, fluid level within the medical device, device pressure, stiffness, and operational load, etc. Such information is presented by the system to the user in real-time to assist in guiding and placing the medical device as desired within the patient. Additionally, measurements may be made by the system post-placement to ensure the medical device is functional and properly placed by interrogating the FBG sensors anew. Further details regarding these and other embodiments are given hereafter.

Note that, though the below discussion focuses on the placement of a catheter assembly into the body of the patient, the placement system described herein can be employed to place a variety of medical devices and components including other elongate and non-elongate medical devices in a variety of locations within the patient body. As such, the principles of the present disclosure should not be considered limiting to what is explicitly described herein.

Examples of catheter assemblies and medical devices that may benefit from the present disclosure include a peripherally-inserted central catheter ("PICC"), central venous catheter ("CVC"), urinary catheter, midline catheter, peripheral catheter, an ECG lead, a needle, an NG tube, etc.

In light of the above, the optical fiber-based strain sensor system described above thus serves as one modality in the above-introduced medical device placement system for guiding and placing a medical device within the body of a patient. As such, this modality if also referred to herein as an "optical modality." Note however that the placement system can also employ additional modalities for improving medical device placement accuracy, in addition to the optical modality introduced above and described in further detail below. In one embodiment an additional ultrasound ("US") modality is also employed by the system to enable ultrasound-assisted guidance for introducing a catheter assembly (or other medical device) into the patient's vasculature. After such introduction to the vasculature, the optical modality to be described herein can thereafter be employed to guide the catheter assembly to a desired location within the vasculature. These modalities are described in further detail below. In one embodiment, the optical modality alone is employed by the system.

In yet another embodiment, additional modalities may be employed by the system to assist in guiding a catheter assembly (or other medical device) to a desired destination within the body of the patient. These include a tip location/navigation system ("TLS") modality, wherein magnetically-based tracking of the catheter tip during its advancement through the tortuous vasculature path is employed to detect and facilitate correction of any tip malposition during such advancement; and an ECG modality, wherein ECG signal-based catheter tip guidance is employed to enable tracking and guidance of the catheter tip to a desired position with respect to a node of the patient's heart from which the ECG signals originate. Such ECG-based positional assistance is also referred to as "tip confirmation." Further details regarding these modalities can be found in U.S. Pat. No. 8,781,555, filed Mar. 2, 2010, and titled System for Placement of a Catheter Including a Signal-Generating Stylet," which is incorporated herein by reference in its entirety.

Use of the optical modality according to one embodiment enables the catheter placement system to facilitate catheter placement within the patient's vasculature with a relatively high level of accuracy, i.e., placement of the distal tip of the catheter in a predetermined and desired position. In one example implementation, use of the optical modality may result in correct tip placement being confirmed without the need for a confirmatory X-ray. This, in turn, reduces the patient's exposure to potentially harmful x-rays, the cost and time involved in transporting the patient to and from the x-ray department, costly and inconvenient catheter repositioning procedures, etc.

Figure 1B:
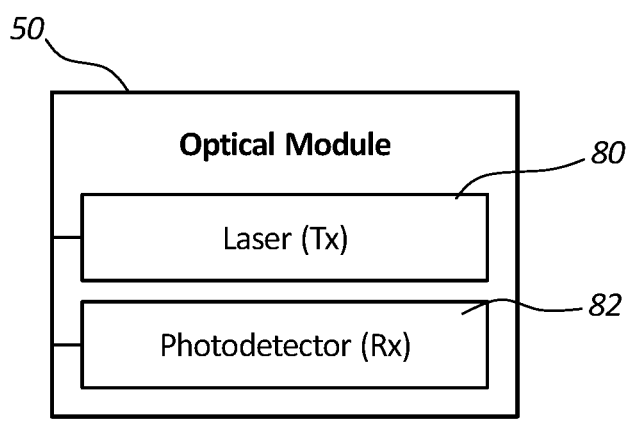
Figure 2:
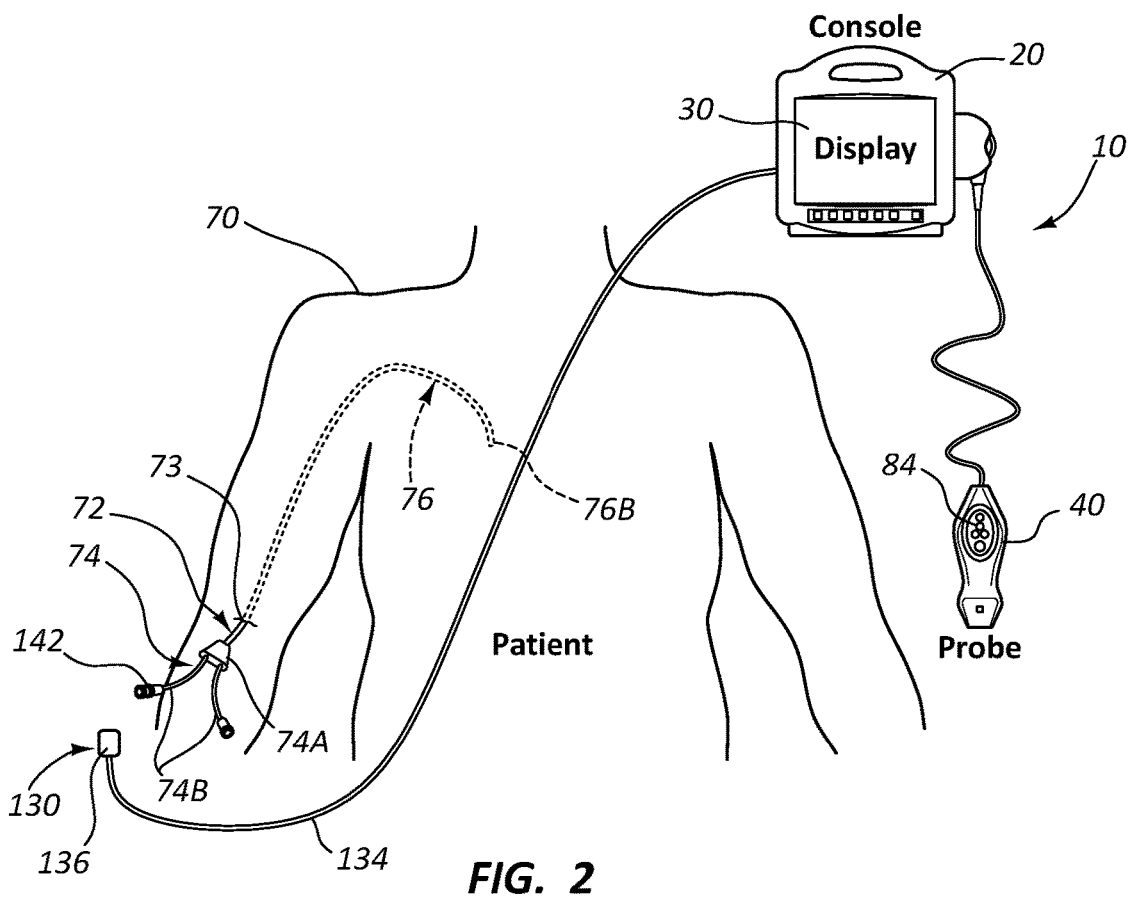
FIG. 2 is a simplified view of a patient and the placement system of FIGS. 1A and 1B.

Reference is first made to FIGS. 1A-2, which depict various components of a placement system ("system"), generally designated at 10, configured in accordance with one example embodiment of the present invention. As shown, the system 10 generally includes a console 20, display 30, probe 40, and optical module 50, each of which is described in further detail below.

FIG. 2 shows the general relation of these components to a patient 70 during a procedure to place a catheter 72 into the patient vasculature through a skin insertion site 73. FIG. 2 shows that the catheter 72 generally includes a proximal portion 74 that generally remains exterior to the patient and a distal potion 76 that generally resides within the patient vasculature after placement is complete. The system 10 is employed to ultimately position a distal tip 76A of the catheter 72 in a desired position within the patient vasculature. In one embodiment, the desired position for the catheter distal tip 76A is proximate the patient's heart, such as in the lower one-third ($\frac{1}{3}^{rd}$) portion of the Superior Vena Cava ("SVC"). Of course, the system 10 can be employed to place the catheter distal tip in other locations. The catheter proximal portion 74 further includes a bifurcation hub 74A that provides fluid communication between the one or more lumens of the catheter 72 and one or more extension legs 74B extending proximally from the bifurcation hub. Note that the bifurcation hub can include one, two, or more fluid paths to fluidly connect the catheter lumens with the corresponding extension legs 74B.

An example implementation of the console 20 is shown in FIG. 2, though it is appreciated that the console can take one of a variety of forms. FIG. 1A shows that a processor 22, including non-volatile memory such as EEPROM for instance, is included in the console 20 for controlling system function during operation of the system 10, thus acting as a control processor. A digital controller/analog interface 24 is also included with the console 20 and is in communication with both the processor 22 and other system components to govern interfacing between the probe 40, optical module 50, and other system components.

The system 10 further includes ports 52 for connection with the optical module 50 and optional components 54 including a printer, storage media, keyboard, etc. The ports in one embodiment are USB ports, though other port types or a combination of port types can be used for this and the other interfaces connections described herein. A power connection 56 is included with the console 20 to enable operable connection to an external power supply 58. An internal battery 60 can also be employed, either with or exclusive of an external power supply. Power management circuitry 59 is included with the digital controller/analog interface 24 of the console to regulate power use and distribution.

The display 30 in the present embodiment is integrated into the console 20 and is employed as a user interface to display information to the clinician during the catheter placement procedure. In another embodiment, the display may be separate from the console. As will be seen, the content depicted by the display 30 changes according to which mode the catheter placement system is in: optical, US, or other modality. In one embodiment, a console button interface 32 and buttons included on the probe 40 can be used to immediately call up a desired mode to the display 30 by the clinician to assist in the placement procedure. In one embodiment, information from multiple modes, such as optical and US, may be displayed simultaneously. Thus, the single display 30 of the system console 20 can be employed for ultrasound guidance in accessing a patient's vasculature and optical modality-based guidance during catheter advancement through the vasculature. In one embodiment, the display 30 is an LCD device.

The probe 40 is employed in connection with the first modality mentioned above, i.e., ultrasound ("US")-based visualization of a vessel, such as a vein, in preparation for insertion of the catheter 72 into the vasculature. Such visualization gives real time ultrasound guidance for introducing the catheter into the vasculature of the patient and assists in reducing complications typically associated with such introduction, including inadvertent arterial puncture, hematoma, pneumothorax, etc.

The handheld probe 40 includes a head that houses a piezoelectric array for producing ultrasonic pulses and for receiving echoes thereof after reflection by the patient's body when the head is placed against the patient's skin proximate the prospective insertion site 73 (FIG. 2). The probe 40 further includes a plurality of control buttons, which can be included on a button pad. In the present embodiment, the modality of the system 10 can be controlled by the control buttons, thus eliminating the need for the clinician to reach out of the sterile field, which is established about the patient insertion site prior to catheter placement, to change modes via use of the console button interface 32.

As such, in one embodiment a clinician employs the first (US) modality to determine a suitable insertion site and establish vascular access, such as with a needle or introducer, then with the catheter. The clinician can then seamlessly switch, via button pushes on the probe button pad 82, to the optical modality without having to reach out of the sterile field. Again, the optical modality can be used to assist in advancement of the catheter 72 through the vasculature toward an intended destination.

FIG. 1 shows that the probe 40 further includes button and memory controller 42 for governing button and probe operation. The button and memory controller 42 can include non-volatile memory, such as EEPROM, in one embodiment. The button and memory controller 42 is in operable communication with a probe interface 44 of the console 20, which includes a piezo input/output component 44A for interfacing with the probe piezoelectric array and a button and memory input/output component 44B for interfacing with the button and memory controller 42.

The handheld ultrasound probe 40 is employed to enable US visualization of the peripheral vasculature of a patient in preparation for transcutaneous introduction of the catheter. In the present example embodiment, however, the probe is also employed to control functionality of other modalities of the system 10, including the optical modality, when navigating the catheter toward its desired destination within the vasculature as described below. Again, as the probe 40 is used within the sterile field of the patient, this feature enables functionality of any one of the modalities to be controlled entirely from within the sterile field. Thus the probe 40 is a multi-purpose device, enabling convenient control of both US and other modality functionality of the system 10 from the sterile field. Note that additional or fewer components can be included with the system 10 than what is shown and described herein.

As mentioned, the system 10 includes the optical module 50, which is shown in further detail ion FIG. 1B. As shown, the optical module 50 includes an optical transmitter, such as a laser 80, configured to produce outgoing optical signals incident on a plurality of optical fiber-based strain sensors (described further below) of the catheter assembly. The optical module 50, as well as an optical receiver, such as a photodetector 82, configured to receive return optical signals from the optical fiber-based strain sensors of the catheter assembly. In one embodiment, the laser 80 is a tunable swept laser and both the laser 80 and the photodetector 82 are operably connected to the processor 22 of the system 10 (FIG. 1A), which governs their operation. In another embodiment, another suitable light source can also be employed in addition to a laser, including semi-coherent light sources, LED light sources, etc.

FIG. 1A also shows that the optical module in the present embodiment is operably connected to a stylet 130, which includes an optical fiber and the plurality of strain sensors, as will be described further below. The stylet 130 is configured to be removably received within the catheter 72 during the procedure to place the catheter into the vasculature of the patient and enable the system 10 to guide the catheter distal tip 76B to a desired destination within the body. Note, however, that the optical fiber and strain sensors can be configured in other ways other than a stylet, some of which are discussed further below. Note further that the optical module 50 can include other components and be included within the system 10 in other configurations apart from what is shown and described herein.

Figure 3:
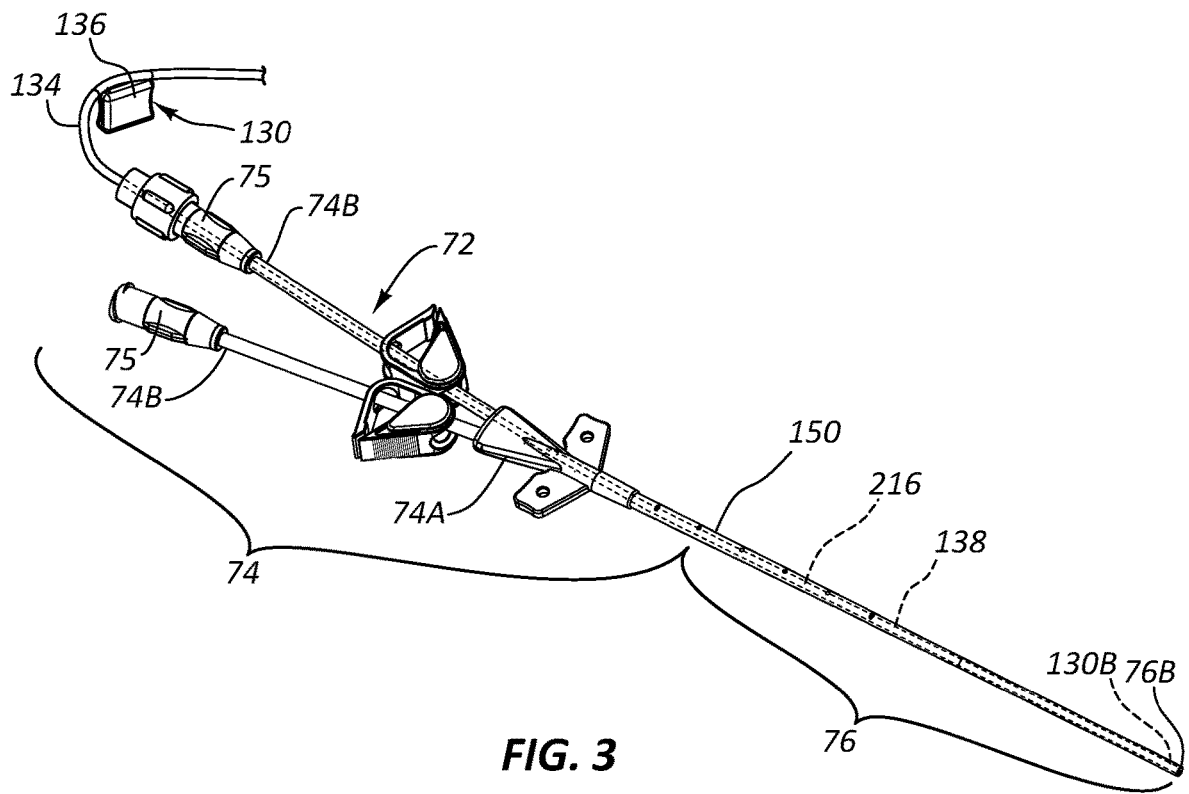
FIG. 3 is a perspective view of a catheter assembly including an optical fiber-based sensor assembly.

FIG. 2 shows the stylet 130 in place within the catheter 72 as the catheter is being inserted into the patient 70 with the assistance of the system 10. FIGS. 2 and 3 depict further details regarding the stylet 130 and the catheter 72. As shown, the catheter 72 includes an elongate catheter tube 150 defining one or more lumens 216 extending between proximal and distal ends of the catheter tube, which are in communication with the corresponding extension legs 74B via the bifurcation hub 74A, as described further above. In the illustrated embodiment the catheter 72 includes two lumens 216 and two corresponding extension legs 74B, though other numbers of lumens and extension legs are possible. Luer connectors 75 are included on the proximal ends of the extension legs 74B.

Figure 9:
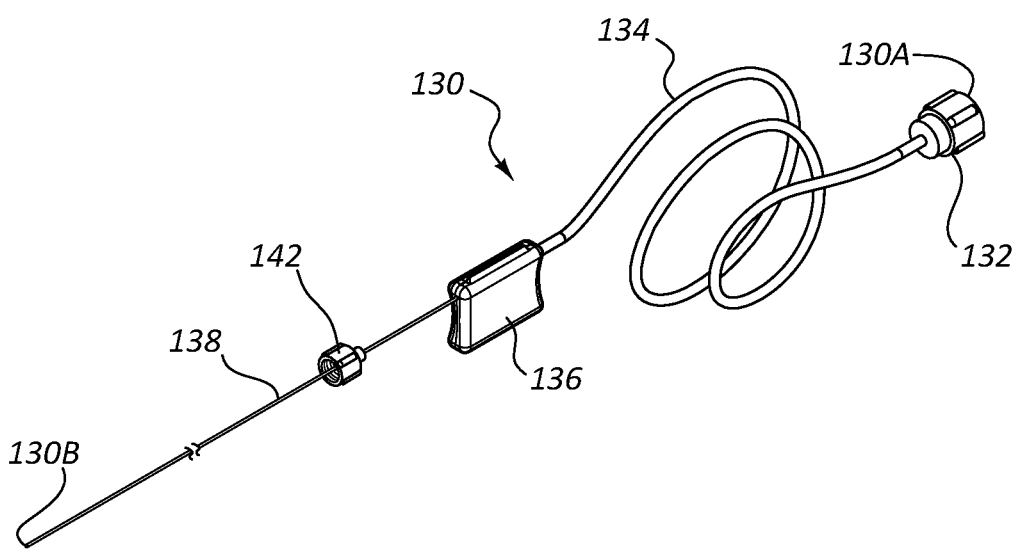
FIG. 9 is a perspective view of a stylet.

Along with FIGS. 2 and 3, reference is made to FIG. 9, which together depict details regarding the stylet 130 and the catheter 72. As shown, the stylet 130 is an elongate device and includes a system connector 132 on its proximal end 130A to enable the stylet to operably connect with the console 20 (FIG. 2) or other suitable component of the system 10 via a threading (or other suitable) engagement. A tether 134 distally extends between the system connector 132 to a catheter connector 142 configured to threadably engage (or otherwise connect with) the luer connector 75 of one of the extension legs 74B of the catheter 72, as seen in FIG. 3. A fiber-bearing portion 138 of the stylet 130 extends distally from the catheter connector 142 to a distal end 130B of the stylet. A handle 136 is included with the tether 134 to assist with manipulation of the stylet 130 by the user during system operation.

Figure 6:
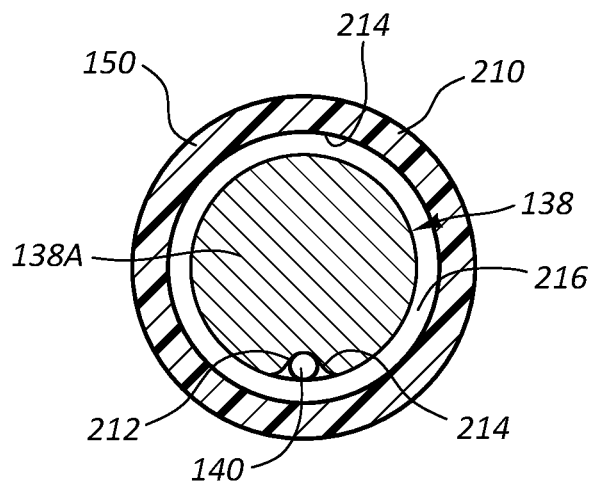
FIG. 6 is a cross sectional view of a catheter tube and a stylet inserted therein.

In greater detail, the fiber-bearing portion 138 includes, as seen in FIG. 6, an elongate core wire 138A with an optical fiber 140 disposed in a longitudinal notch defined along an outer surface thereof. So configured, the core wire 138A and optical fiber 140 extend distally from the catheter connector 142 to the distal end of the stylet 130 (FIG. 9). The optical fiber 140 is secured within the notch of the core wire 138A by potting 214 (such as an adhesive), or by other suitable mode. The core wire 138A includes a suitable, flexible material, including stainless steel for instance. FIG. 6 shows the fiber-bearing portion 138 disposed in a lumen 216 defined by a wall 210 of a single-lumen catheter tube 150, though it is appreciated that the size, shape, and other configuration of the fiber-bearing portion 138 can vary from what is shown and described herein in order to accommodate catheters, lumens, and medical devices of differing configurations.

As shown in FIG. 2, the stylet 130 is inserted into the catheter 72 during use of the system 10 to place the catheter 72 in the body of the patient 70. The stylet 130 is shown with the fiber-bearing portion 138 disposed in the lumen of the catheter 72 and the tether 134 extending from the fiber-bearing portion to the console 20 such that the stylet is operably connected to the system 10 (via the stylet system connector 132). In this way, outgoing optical signals produced by the laser 80 (FIG. 1B) of the optical module 50 and return optical signals to be received by the photodetector 82 can travel to and from the optical fiber 140 (FIG. 6) and its corresponding strain sensors, as will be discussed further below.

FIG. 3 depicts the manner of operable connection of the stylet with the catheter 72. As shown, the fiber-bearing portion 138 is disposed within one of the lumens 216 of the catheter tube 150 such that the distal end of the stylet 130B—and the distal end of the fiber-bearing portion and accompanying optical fiber 140—is substantially co-terminal with the distal tip 76B of the catheter. The fiber-bearing portion 138 extends proximally up the lumen 216, through the bifurcation hub 74A and corresponding extension leg 74B to the catheter connector 142, which is shown threadably attached to the luer connector 75 of the extension leg. The tether 134 is further shown extending from the catheter 72 to operably connect with the console 20, as shown in FIG. 2. This connective configuration is used during the procedure to insert the catheter 72 into the body of the patient 70, and in one embodiment the stylet is pre-loaded into the catheter during time of catheter manufacture or prior to commencement of the insertion procedure. It is appreciated that the stylet 130, the fiber-bearing portion 138, and the optical fiber 140 can be configured in other ways while still enabling the desired functionality of the system 10 to be performed. In yet another embodiment, the optical fiber 140 need not be substantially co-terminal with the distal tip 76B of the catheter 72, but can terminate proximal or distal thereto, as may be appreciated by one skilled in the art. As will be seen, the strain sensors of the optical fiber 140 included with the fiber-bearing portion 138 of the stylet 130 enable the catheter 72 to be tracked during its advancement through the patient vasculature.

Note further that, though described herein as a stylet, in other embodiments a guidewire or other catheter guiding apparatus could include the components and functionality described herein. Indeed, it should appreciated that "stylet" as used herein can include any one of a variety of devices configured for removable placement within a lumen of the catheter (or other portion of a medical device) to assist in placing a distal end of the catheter in a desired location within the patient's vasculature. Also, note that other connection schemes between the stylet 130 and the system 10/console 20 can also be used without limitation.

Note that a sterile drape is often positioned over the patient 70 during the catheter insertion procedure in order to define the majority of a sterile field: areas above the drape are sterile, while areas below (excluding the insertion site and immediately surrounding region) are non-sterile. For instance, areas and components above the drape and proximate to the insertion site 73 (including the catheter 72, the stylet 130, and tether 134) are included in the sterile field, while areas and components below the drape, including the patient's chest and regions immediately surrounding the patient 70 are considered a non-sterile field. In cases where the tether 134 of the stylet 130 needs to penetrate the drape in order to pass between the sterile and non-sterile fields, suitable connection nodes can be included with the stylet in order to pierce the drape while not compromising the sterile field. U.S. Pat. No. 8,781,555, incorporated by reference above, includes various examples of drape-piercing embodiments that can be employed to enable the stylet to acceptably pass through the drape while still enabling outgoing and return optical signals, as well as other signals, to pass between the optical fiber 140 and the console 20.

Figure 4:
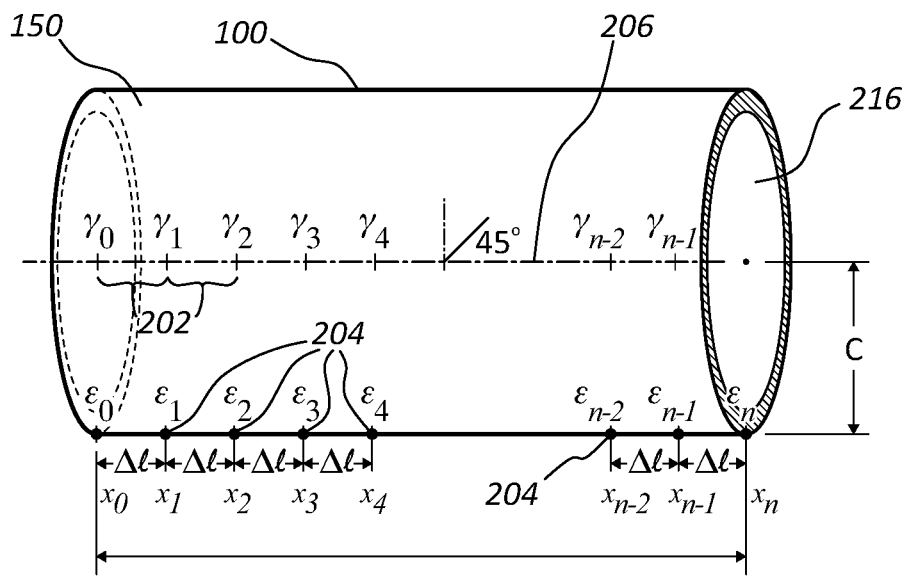
FIG. 4 is a side view of a portion of a catheter tube of the catheter assembly of FIG. 3.

FIG. 4 generally depicts a portion, or structure 100, of the catheter tube 150 of the catheter 72 to depict the spatial relationship between the catheter tube and the strain sensors included with the optical fiber 140 discussed above. As shown, the structure 100 is subdivided into a plurality of sections 202 (also designated with $\gamma_i$ (i=0, 1, 2, 3, . . . n) such that the sections are designated as $\gamma_0, \gamma_1, \ldots \gamma_n$), each section having a length $\Delta 1$, wherein strain sensors 204 are positioned at the junction of each adjacent section 202, as well as at the beginning and end of the sections, designated in FIG. 4 as $x_i$, thus at $x_0, x_1 \ldots, x_n$. The strain sensors 204 are positioned a distance c from a neutral axis of 206 of the catheter tube 150. When operative, the strain sensors 204 are capable of each detecting a corresponding strain c such that strain $\epsilon_0$ is detected at strain sensor 204 positioned at $x_0$ at the junction for section $\gamma_0$, etc. U.S. Pat. No. 7,715,994, incorporated herein by reference in its entirety, gives further details regarding the strain sensors and their spatial distribution as depicted in FIG. 4.

Figure 7:
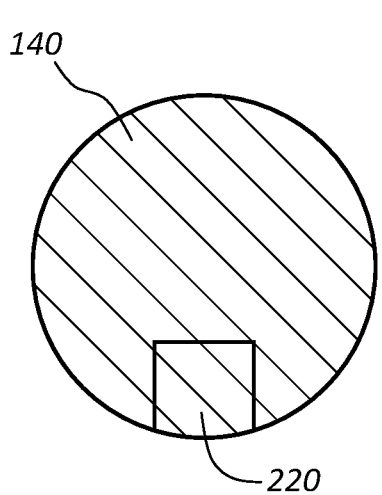
FIG. 7 is a cross sectional view of an optical fiber with a single sensor position region.
Figure 8:
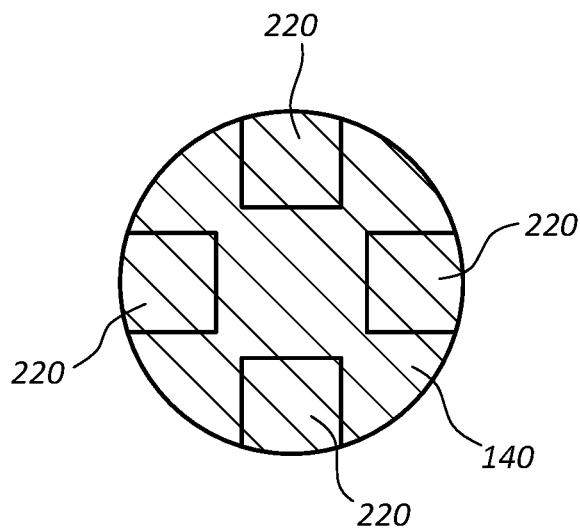
FIG. 8 is a cross sectional view of an optical fiber with multiple sensor positions.

FIG. 7 shows that, in one embodiment, a predetermined sensor position region 220 is defined within the optical fiber 140, wherein the sensors 204 are disposed along the longitudinal length of the optical fiber. In another embodiment, multiple sensor position regions 220 can be defined within the single optical fiber 140, as shown in FIG. 8, for instance, such that distinct series, or channels, of strain or other sensors can be included on a single optical fiber. These multiple, non-colinear channels of strain sensors can be employed for differing purposes, such as one or more series to indicate medical device position with another series to monitor temperature along the medical device, for instance. These and other strain sensor position configurations with the optical fiber are therefore contemplated.

Figure 5:
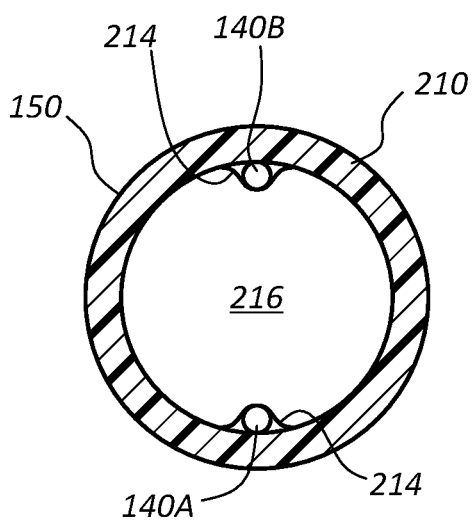
FIG. 5 is a cross sectional view of a catheter tube.

The strain sensors 204 in one embodiment can be included with an optical fiber that is in turn included in a fiber-bearing of a stylet, such as the stylet 130 described above in connection with FIGS. 3, 6, and 9. In another embodiment, the strain sensors 204 are included with an optical fiber that is permanently incorporated into the catheter tube 150, such as is seen in FIG. 5. Many other possible strain sensor implementations are possible, including other types of fiber optic sensors.

In the present embodiment, the strain sensors 204 are configured as fiber Bragg grating ("FBG") sensors. The FBG sensors 34 are each configured to detect strain of the optical fiber at each sensor location, thus enabling the shape and movement of the optical fiber, and thus the catheter tube 150 with which it is included, to be detected and determined as the catheter is inserted into the body of the patient 70, as explained immediately below.

In greater detail, once the catheter 72 has been introduced into the patient vasculature via the insertion site 73 (FIG. 1) the optical modality of the system 10 can be employed to advance the catheter distal tip 76A toward its intended destination proximate the SA node, in the current embodiment, noting that other intended destinations are also possible. The catheter 72 carries within one of its lumens 216 the stylet 130 including the fiber-bearing portion 138, which in turn includes the optical fiber 140 with its strain sensors 204 (e.g., the FBG sensors in the present embodiment). As the stylet-loaded catheter 72 is advanced toward the patient's heart, outgoing optical signals are produced by the laser 80 of the optical module 50 (FIGS. 1A, 1B), which optical signals propagate distally through the optical fiber 140 via the stylet tether 134 to interrogate each of the FBG-type sensors 204, resulting in return optical signals from the sensors. The return optical signals from the FBG-type sensors 204 are received by the photodetector 82 of the optical module after travelling proximally through the optical fiber 140 and the stylet tether 134, which are then forwarded to the processor 22. The outgoing optical signal interrogation and return optical signal process is iterated at a scan rate to provide real-time monitoring. In one embodiment scan rates of 24 scans per second are employed, though other rates are possible. Specified algorithms and processes are followed to determine from the return optical signals the strain data from each of the FBG-type sensor 204. Further information regarding the algorithms and processes referred to immediately above, including serial multiplexing, suitable wavelength division multiplexing ("WDM"), and optical frequency domain reflectometry ("OFDM") processes with regard to a fiber optic sensing system ("F.O.S.S.") is described in: U.S. Pat. No. 7,520,176; U.S. Pat. No. 7,715,994; U.S. Pat. No. 8,700,358; and U.S. Pat. No. 8,909,040, each of which is incorporated herein by reference in its entirety.

In one embodiment and in light of the above, therefore, a method for placing a catheter assembly (or other medical device) into a body of a patient includes stages: propagating an outgoing optical signal to a plurality of optical fiber-based strain sensors included with the catheter assembly; receiving a return optical signal from the strain sensors; and processing the return optical signal received from the strain sensors to derive data relating to the medical device. These stages are successively repeated while inserting the catheter assembly into the body of the patient so as to guide the catheter assembly to its intended destination.

This above-described process results in specified strain data to be correlated along the sensor-equipped length of the optical fiber 140. In turn, given the disposal of the optical fiber 140 within the lumen 216 of the catheter tube 150, the strain data enables information regarding the two- and three-dimensional shape of the catheter tube 150 within the patient of the patient 70 to be ascertained, given that the detected strain-related displacement, bending, pressure, and torsion/twisting of the optical fiber 140 correlates to the catheter tube itself in which the optical fiber is disposed. This and other informational aspects relating to the data collected from the sensors 204 can be communicated to the user of the system 1, via the display 30 and/or other suitable user interface mode, to assist the user in knowing the location, orientation and shape of the catheter 72 within the patient vasculature, thus enabling the user to advance the catheter distally and position the distal tip 76B of the catheter in a desired location therein, in part by the fact that the distal end of the sensor-equipped optical fiber 140 is substantially co-terminal with the distal tip of the catheter within the vasculature, in the present embodiment. The process of sending and receiving outgoing and return optical signals, respectively, occurs iteratively during system operation such that position, orientation, and shape information relating to the catheter 72 is continuously received by the user via the system 10 during the catheter placement procedure.

Once it has been positioned as desired using the system 10 as just described, the catheter 72 may be secured in place and the stylet 130 removed from the catheter lumen. It is noted here that the stylet may include one of a variety of configurations in addition to what is explicitly described herein. In one embodiment, the stylet can attach directly or indirectly to the console. In another embodiment, the optical fiber of the stylet can be integrated into the catheter structure itself, thus eliminating the need for the stylet in bearing the optical fiber and included strain sensors. FIG. 5 gives one example of such an embodiment, wherein the catheter tube 150 includes first and second optical fibers 140A, 140B that are each affixed to an inner surface of the tube wall 210 that defines the lumen 216. A potting 214, such as an adhesive, is used to adhere the optical fibers 140A, 140B to the tube wall 210. One, two, or more optical fibers can be included in the catheter tube in this manner. Also, in one embodiment, the optical fiber can incorporated into the catheter wall itself, such as via a co-extrusion process, for instance. These and other variations are therefore contemplated.

Note that in one embodiment the console 20 includes the electronic components, such as the processor 22 (FIG. 1), necessary to process the return optical signals received by the photodetector 82 via the stylet 130 or other suitable structure including the optical fiber 140 and sensors 204. In another embodiment, this functionality can be included in another system component including, for example, the optical module 50.

In the present embodiment, the position, orientation, shape, and other information regarding the catheter 72, as provided by the optical fiber-based sensors 204 and as described above is communicated to the user of the system 10 to assist with placing the distal tip 76B (or other portion of the catheter) at a desired location within the patient vasculature/body, such as the lower $\frac{1}{3}^{rd}$ of the superior vena cava. In the present embodiment, such information is depicted on the display 30, included on the console 20 as part of the system 10, though it can be configured in other ways as well, including as a separate component in one embodiment. As has been described further above, the functionality of the display 30 can be controlled by control buttons 84 included on the handheld probe 40 (FIGS. 1A, 2), thus eliminating the need for the clinician to reach out of the sterile field (such as touching the button interface 32 of the console 20) to change modes. Thus, in the present embodiment the probe 40 is employed to also control some or all functionality of the system 10. Note that the button interface 32 or other input configurations can also be used to control system functionality. Also, in addition to the visual display 30, aural information, such as beeps, tones, etc., can also be employed by the system to assist the clinician during catheter placement. Moreover, the buttons included on the probe 40 and the console button interface 32 can be configured in a variety of ways, including the use of user input controls in addition to buttons, such as slide switches, toggle switches, electronic or touch-sensitive pads, etc.

Figure 10A:
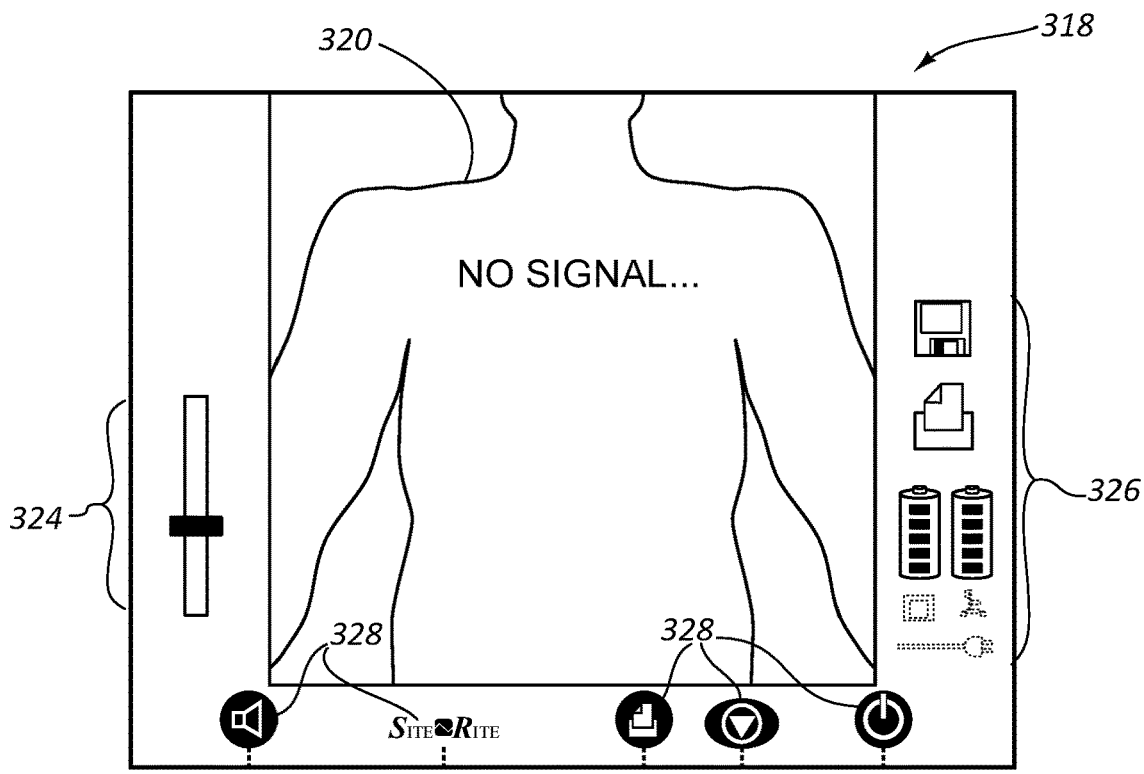
FIGS. 10A-10C depict various screenshots of the placement system of FIGS. 1A and 1B.

FIG. 10A shows an example screenshot 318 as depicted on the display 30 while the system 10 is in operation. A representative body image 320 is shown. Other information is provided on the display screenshot 318, including a depth scale indicator 324, status/action indicia 326, and icons 328 corresponding to the button interface 32 included on the console 20 (FIG. 1A). Though the icons 328 in the present embodiment are simply indicators to guide the user in identifying the purpose of the corresponding buttons of the button interface 32, in another embodiment the display can be made touch-sensitive so that the icons themselves can function as button interfaces and can change according to the mode the system is in.

Figure 10B:
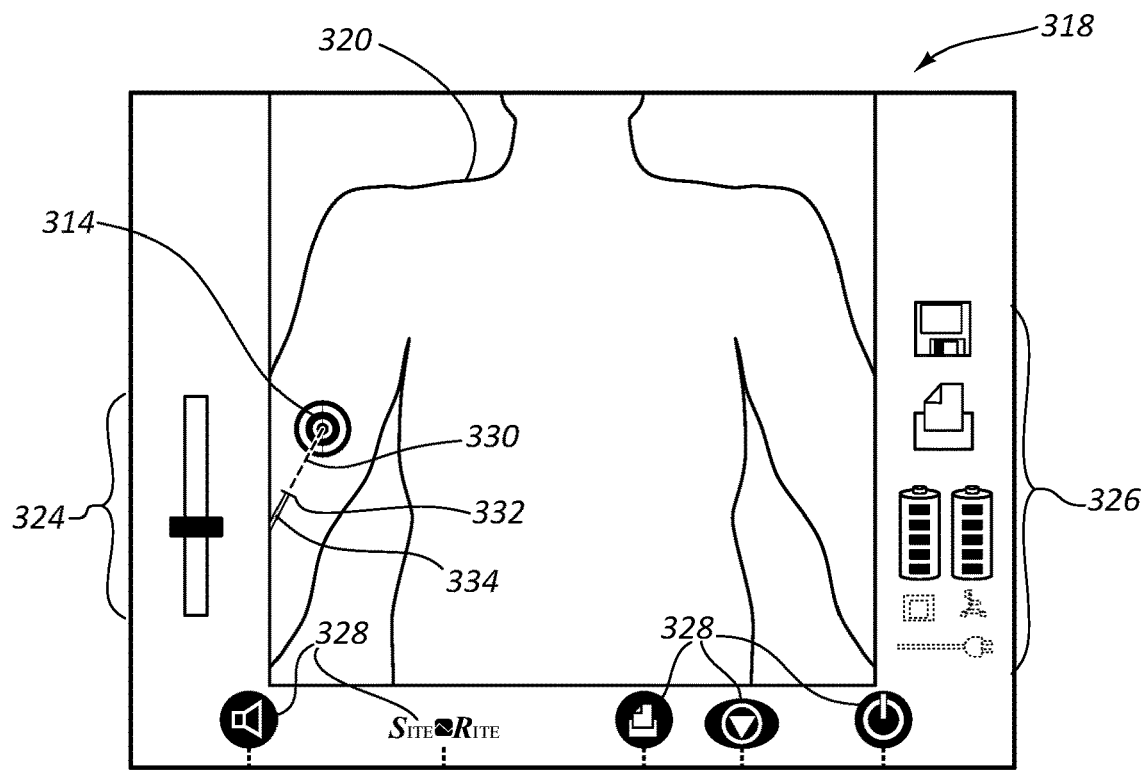

During initial startup and preparation for insertion of the catheter 72 into the patient vasculature, the display screenshot may indicate "no signal," as seen in FIG. 10A, indicating that no data is being returned from the sensors 204 of the optical fiber 140. In FIG. 10B, a distal portion of the catheter 72 has been inserted into the body of the patient 70, which is represented in the screenshot 318 by a relatively short path of travel 330 distal to a depicted insertion site 332 (which corresponds to the actual insertion site 73 of FIG. 2) on the display 30. A still-external portion 334 of the catheter is also shown on the screenshot 318 of FIG. 10B, proximal to the depicted insertion site 332. Temperature-based differences as detected in data received from the return optical signals enables the system 10 to determine at which point along the length of the optical fiber 140 the catheter tube 150 has entered into the body 70 of the patient in the present embodiment, thus enabling the system to depict the location of the insertion site 332. In like manner, the internal path of travel 330 and the external portion 334 can be depicted on the display. A position icon 314 is also depicted at the detected distal end of the sensor-equipped optical fiber 140, corresponding to the distal tip 76B of the catheter 72, in the present embodiment.

Figure 10C:
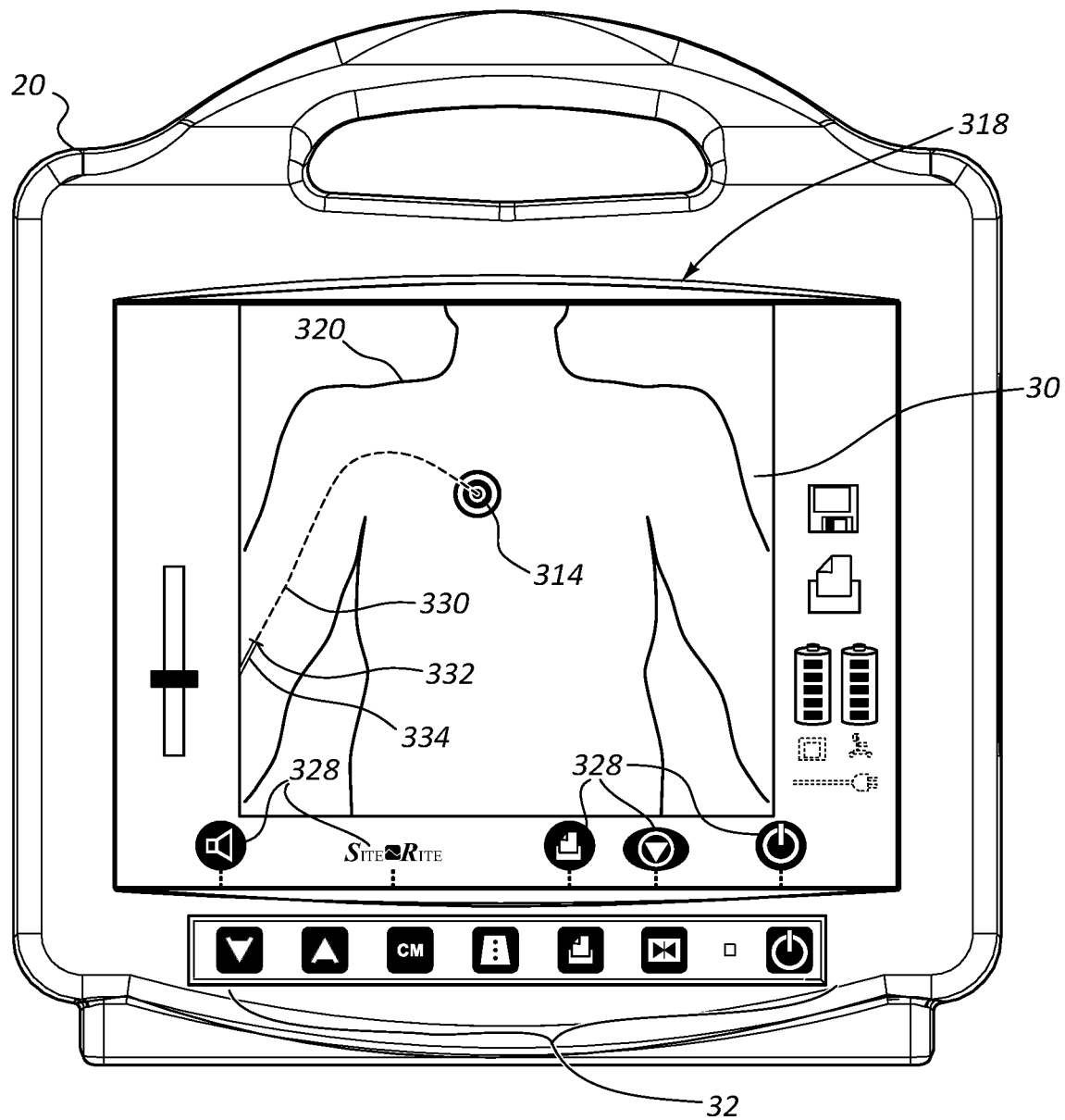

In FIG. 10C, the catheter 72 has advanced proximate a desired position within the patient vasculature, i.e., proximate the lower $\frac{1}{3}^{rd}$ portion of the SVC in the present embodiment, as indicated by the position icon 314 on the screenshot body image 320. This is indicated by the relatively longer internal path of travel 330 with respect to the insertion site 332. The system 10 is further able to detect and depict any bends or changes in direction in the catheter via processing of the return optical signals from the various sensors 204 along the length of optical fiber disposed in one of the lumens 216 of the catheter tube 150 (FIG. 3). As such, position, shape, and orientation of the catheter 72 is determined by the system 10 and communicated to the clinician via the display 30, thus enabling the clinician to accurately guide the catheter to the desired position within the vasculature.

In one embodiment it is appreciated that the mapping of the catheter as an image on the body image 320 to indicate the actual location of the catheter 72 within the actual body of the patient 70 is enabled by knowledge of the insertion site of the catheter (i.e., a reference location) —here represented by the insertion site 332 of FIG. 10C, the length of the portion of the catheter found inside the patient body (represented by the internal portion of the catheter 330), and the shape/displacement of the catheter as detected by the optical fiber-based sensors 204 disposed within the catheter.

Figure 11:
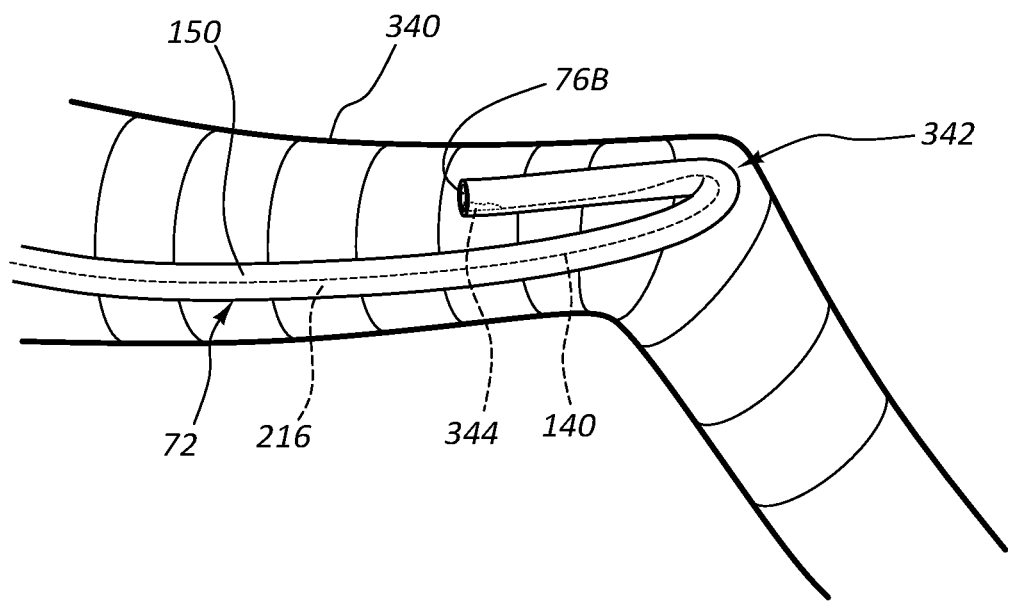
FIG. 11 is a cross sectional view of a vessel of a body of a patient with a catheter tube disposed therein.

FIG. 11 depicts a scenario where optical modality of the system 10 can assist a clinician in detecting a malposition scenario for the catheter 72 within the vasculature. As shown, the catheter tube 150 is disposed within a vessel 340 of the patient 70 in such a way as to undesirably double back on itself and form a kink region 342. Such kinks are possible during insertion of the catheter 72 into the body. The optical fiber 140, including the plurality of FBG-type sensors 204, is also shown running along the length of the lumen defined by the catheter tube 150. Return optical signals from the sensors 204 in the kink region 342 during system operation will indicate the strain in the optical fiber 140 caused by the kink. After processing by the system 10, information relating to the kink can be communicated to the clinician via the display 30 or by other suitable means. In one example, for instance, the clinician can view the catheter tube doubling back on itself as depicted on the display. Once the kink condition has been identified, the clinician can correct the kink and proceed with catheter insertion.

FIG. 11 further shows an obstruction 344, such as a thrombus or fibrin sheath, present proximate the distal end 76B of the catheter tube 150. Such obstructions are also detectable by sensors 204 of the optical fiber 140 as part of the optical modality of the system 10. Once the obstruction condition has been communicated to the clinician, corrective measures may be undertaken to clear the obstruction from the catheter tube 150.

It should be appreciated that the use of optical fiber-based sensors can be employed to confirm that a previously inserted catheter assembly (or other medical device) is still positioned as desired within the body of the patient. In one embodiment, this is achieved by feeding a stylet including an optical fiber-based series of strain sensors distally within a lumen of the catheter until reaching the distal tip of the catheter. Strain and other measurements may then be performed by the sensors disposed within the catheter lumen, thus enabling the system with which the sensors are operably connected to determine the shape, orientation, and position of the catheter tube within the vasculature of the patient, including the termination point of the catheter distal tip. This enables a clinician to ensure the catheter is still positioned at the desired location.

In addition to strain, stress, and torsion measurements that enable the two- and three-dimensional shape, position, and orientation of the catheter or other medical device to be determined while in the patient body, the optical modality described herein can detect and communicate other information to the clinician via the system 10 using the data provided by the sensor interrogation by the outgoing optical signals and the resultant return optical signals. Such information includes temperature, pressure, stiffness, strength, operational load on the catheter tube, liquid level within the lumen 14, blood oxygen level, magnetic field presence, etc. Further, it is appreciated that, in light of the above disclosure, other conditions relating to the catheter may be detected, including malposition/misdirection during catheter advancement including contralateral and U placement, arterial vs. venous placement, venous pressure and core body temperature, confirmation of the catheter staying within the true lumen of the vein or other vessel in the case of navigation through chronic total occlusion or other vessel blockage scenarios, etc.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A catheter assembly, comprising:
   a catheter including an elongate catheter tube defining a portion of at least one lumen through the catheter, the portion of the at least one lumen extending between at least a proximal end and a distal end of the elongate catheter tube;
   a stylet removably inserted into the at least one lumen of the catheter, the stylet comprising:
   a system connector configured to operably connect with a console of a medical device placement system;
   a catheter connector configured to operably connect with at least one Luer connector of the catheter assembly, a fiber-bearing portion of the stylet extending distally from the catheter connector to a distal end of the stylet;
   a tether between the system connector and the catheter connector and a handle with the tether to assist with manipulation of the stylet by a user;
   a hub;
   at least one extension leg;
   the at least one Luer connector, wherein the at least one Luer connector is disposed over a proximal end of the at least one extension leg, wherein the hub provides fluid communication between the elongate catheter tube and the at least one extension leg for the at least one lumen through the catheter; and an optical fiber incorporated into the stylet, the optical fiber having a first plurality of optical fiber-based strain sensors disposed along a first longitudinal portion of the optical fiber and a second plurality of optical fiber-based strain sensors disposed along a second longitudinal portion of the optical fiber, the first plurality of optical fiber-based strain sensors and the second plurality of optical fiber-based strain sensors configured to receive incoming optical signals from an operably connected light source and return outgoing optical signals to an operably connected photodetector for more than one aspect of the optical fiber in accordance with at least the first plurality of optical fiber-based strain sensors and the second plurality of optical fiber-based strain sensors, wherein the fiber-bearing portion of the stylet includes a core wire and the optical fiber, the optical fiber secured in a longitudinal notch of the core wire by potting.

\* \* \* \* \*